United States Patent
Saladin (12)

(10) Patent No.: US 6,644,811 B2
(45) Date of Patent: Nov. 11, 2003

(54) OCULOMOTOR BALANCE TESTER

(75) Inventor: Jimmie James Saladin, Big Rapids, MI (US)

(73) Assignee: Ferris State University, Big Rapids, MI (US)

( * ) Notice: Subject to any disclaimer, the term of this patent is extended or adjusted under 35 U.S.C. 154(b) by 246 days.

(21) Appl. No.: 09/832,555

(22) Filed: Apr. 11, 2001

(65) Prior Publication Data

US 2002/0176051 A1 Nov. 28, 2002

(51) Int. Cl.⁷ .................................................. A61B 3/02
(52) U.S. Cl. ......................................................... 351/239
(58) Field of Search .................................. 351/201, 202, 351/203, 209, 211, 212, 215, 220, 237, 239, 240, 246

(56) References Cited

U.S. PATENT DOCUMENTS

| | | | |
|---|---|---|---|
| 4,222,639 A | 9/1980 | Sheedy | |
| H293 H | 6/1987 | Task et al. | |
| 4,712,895 A | 12/1987 | Kamiyama et al. | |
| 4,887,897 A | 12/1989 | Nose et al. | |
| 4,903,706 A | 2/1990 | Vila-Cora et al. | |
| 5,026,151 A | 6/1991 | Waltuck et al. | |
| 5,094,521 A | 3/1992 | Jolson et al. | |
| 5,214,455 A | 5/1993 | Penney et al. | |
| 5,302,981 A | 4/1994 | Wirtz | |
| 5,309,185 A | 5/1994 | Harper | |
| 5,329,322 A | 7/1994 | Yancy | |
| 5,757,460 A | 5/1998 | Cockley | |
| 5,777,718 A | 7/1998 | Kohayakawa | |
| 5,877,840 A | 3/1999 | Yamada et al. | |
| 5,889,577 A | 3/1999 | Kohayakawa | |
| 5,963,300 A | * 10/1999 | Horwitz | 351/209 |

FOREIGN PATENT DOCUMENTS

DE  19519413  8/1996

OTHER PUBLICATIONS

American Journal of Optometry & Physiological Optics, Copyright © 1986 American Academy of Optometry Symposium Paper by J. James Saladin, College of Optometry, Ferris State College, Big Rapids, MI *Interpretation of Divergent Oculomotor Imbalance Through Control System Analysis* vol. 65, No. 6, pp. 439–447; Jun., 1988.

American Journal of Optometry & Physiological Optics, Copyright © 1983 American Academy of Optometry Symposium Paper by J. James Saladin, College of Optometry, Ferris State College, Big Rapids, MI *Convergence Insufficiencey, Fixation Disparity, and Control Systems Analysis* vol. 63, No. 8, pp. 645–653; Aug., 1986.

American Journal of Optometry & Physiological Optics, Copyright © 1983 American Academy of Optometry Symposium Paper by J. James Saladin and Leland W. Carr, College of Optometry, Ferris State College, Big Rapids, MI *Fusion Lock Diameter and the Forced Vergence Fixation Disparity, Curve* vol. 60, No. 12, pp. 933–943; Dec., 1983.

(List continued on next page.)

Primary Examiner—George Manuel
(74) Attorney, Agent, or Firm—Van Dyke, Gardner, Linn & Burkhart, LLP

(57) ABSTRACT

A diagnostic tool for evaluating a patient's oculomotor system includes tests for measuring the amount of a patient's heterophoria and fixation disparity and determining whether these two measurements bear a normal or abnormal relationship. If the results of these tests do not bear a normal relationship, it is concluded that an oculomotor imbalance or dysfunction exists and further analysis should be performed to determine the precise nature of the dysfunction. The diagnostic tool may comprise a near-point card on which tests for heterophoria and fixation disparity are printed, as well as a graph indicating the expected or normal relationship between the results of these two tests. Additional diagnostic tests may be included on the card.

28 Claims, 3 Drawing Sheets

OTHER PUBLICATIONS

American Journal of Optometry & Physiological Optics, Copyright © 1983 American Academy of Optometry Symposium Paper by J. James Saladin and James E. Sheedy, College of Optometry, Ferris State College, Big Rapids, MI *Population Study of Fixation Disparity, Heterophoria, and Vergence* vol. 55, No. 11, p. 744–750, Nov. 1978.

Saladin JJ., Chapter 20 entitled "Phorometry and Stereopsis," In Benjamin WJ (ed): *Borish's Clinical Refraction*, Philadelphia, 1998, Saunders, pp. 724–773.

Saladin JJ., Chapter 5 entitled "Horizontal Prism Prescription," In Cotter SA (ed): *Clinical Uses of Prism*, St. Louis, 1995, Mosby, pp 109–147.

*Bernell Products Catalog 2000–2001, A Division of Vision Training Products Inc.*, pp. 11, 29, and 33.

The College of Optometrists, Copyright © 2001, written by W. Jaschinski of Dortmund, Germany, *Methods for measuring the proximity–fixation–disparity curve* vol. 21, No. 5, pp. 368–375; 2001. The author of this article is believed to be the same as the inventor of DE19519413.

English language abstract for DE19519413.

* cited by examiner

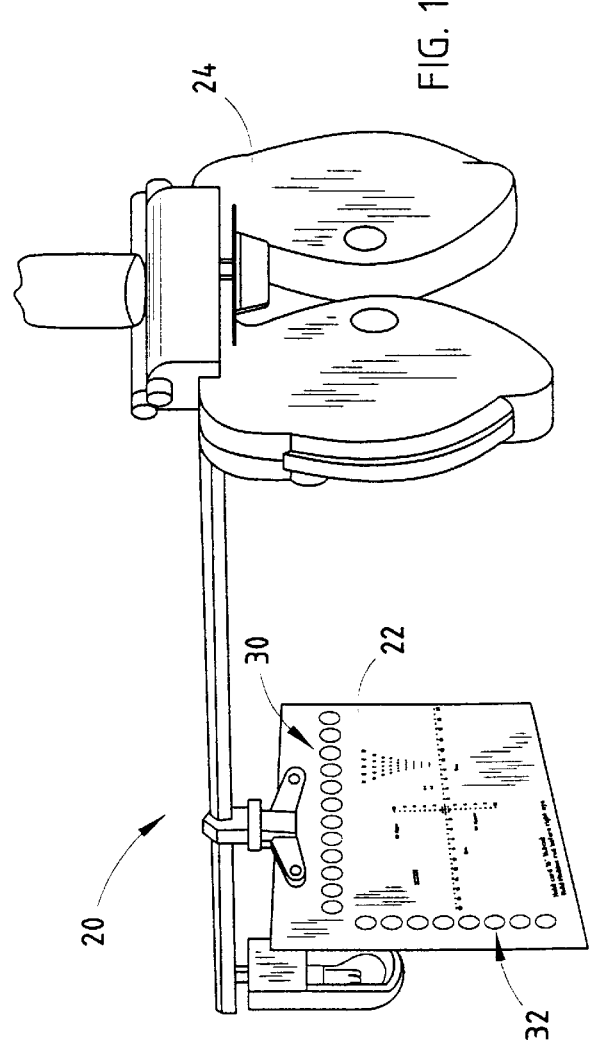
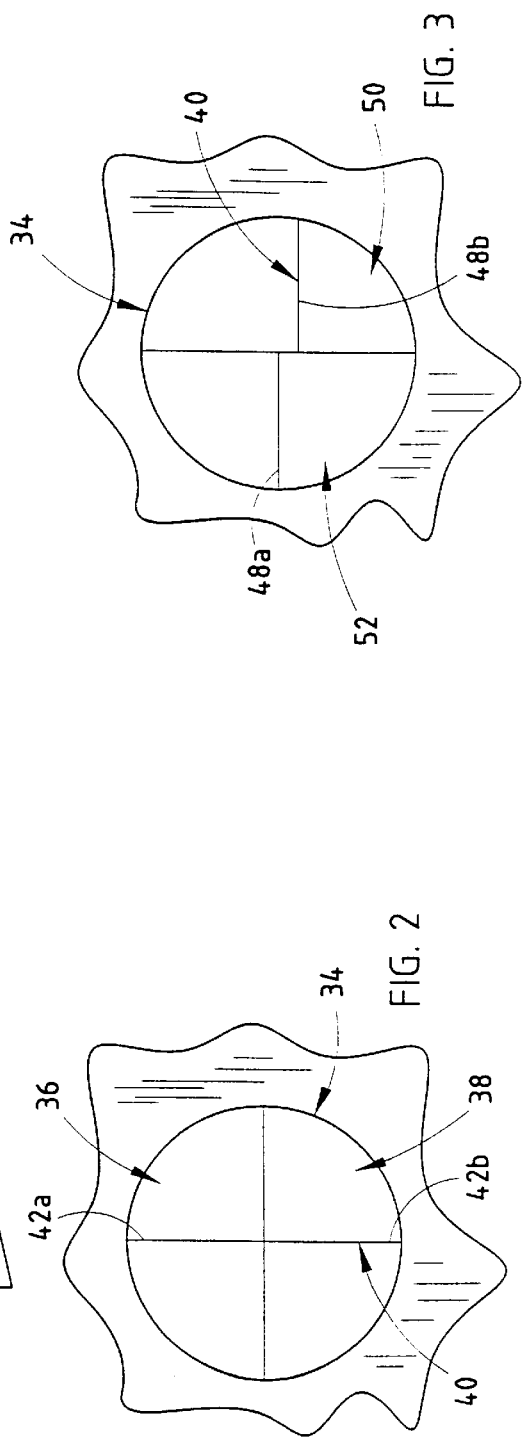

OCULOMOTOR BALANCE TESTER

BACKGROUND OF THE INVENTION

This invention relates generally to a diagnostic tool for evaluating a patient's oculomotor system, and more particularly for determining whether the patient's oculomotor system is in balance or not.

When a person looks at a particular object, there are two major systems that the person's body utilizes in order to ensure that the object is accurately viewed. One of the systems is the accommodative system, which is the system that changes the shape of the lenses in the eyeballs to make sure the images are properly focused on the person's retinas. The other system is the vergence system, which is the system responsible for moving the eyeballs so that they are properly aimed at the object being looked at. Both systems provide a source of innervation, i.e. nerve stimulation, to the oculomotor system. The innervation stimulates the muscles of the eyes in order to change their alignment and focusing so that an object can be viewed correctly. Both the accommodative (focusing) and vergence (aiming) systems can, within certain limits, correct for imperfections in the other system. There is, however, a normal range of innervation that each system comfortably supplies, and when either one of these systems moves outside that normal range, the patient experiences oculomotor dysfunction, or imbalance.

For most conventional eye examinations, there are usually a limited number of standard visual diagnostic tests that are performed. Because of the time-consuming nature of evaluating whether a patient has oculomotor dysfunction, such tests are often not part of the ophthalmic practitioner's standard eye examination. When not diagnosed and treated, however, oculomotor dysfunction can have many adverse effects for the patient, including reading discomfort, burning sensations, sleepiness, or even diplopia, among others. A need therefore exists for a simple diagnostic tool capable of evaluating whether a patient's oculomotor system is in balance or not.

SUMMARY OF THE INVENTION

Accordingly, the present invention provides a simple, efficient diagnostic tool for determining whether a patient's accommodative and vergence systems are in balance or not. According to one aspect of the present invention, a diagnostic tool is provided that includes a first test for measuring a patient's heterophoria and a second test for measuring a patient's fixation disparity. The tool further includes an instrument for determining whether the measured heterophoria and fixation disparity indicate that the patient's accommodative and vergence systems are in balance or not.

According to another aspect of the present invention, a diagnostic tool is provided that includes a base with a front surface. A test for heterophoria and a test for fixation disparity are both positioned on the front surface of the base. An instrument is provided for determining if the patient's measured heterophoria and fixation disparity indicate that the patient's accommodative and vergence systems are in balance or not.

According to still another aspect of the present invention, a method is provided for determining a patient's oculomotor imbalance. The method includes measuring the patient's heterophoria and fixation disparity, and then determining whether the measured amount of the patient's fixation disparity is normal for the measured amount of heterophoria. If it is not, then it is concluded that the patient's oculomotor system is out of balance.

According to still other aspects of the present invention, the tests for heterophoria and fixation disparity may be mounted on a near-point card. The instrument for determining whether the measured amount of fixation disparity is normal or not for a given amount of heterophoria may include a graph printed on the card indicating the normal relationship for fixation disparity and heterophoria. The heterophoria test may be a modified Thorington test. The fixation disparity test may include a plurality of areas containing first and second images that are each positioned behind oppositely polarized materials. By determining when the images appear aligned to the patient, the fixation disparity can be measured. The card may also include additional diagnostic tests for helping to pinpoint the oculomotor imbalance, should such an imbalance be detected.

The present invention provides a quick, cost-effective, and efficient way for determining whether a patient's oculomotor system is in balance or not. Because the invention can be performed so easily, it readily can be implemented into standard eye-examinations, thereby allowing proper treatment to be given to those individuals suffering from oculomotor dysfunction. These and other advantages of the present invention will be apparent to one skilled in the art in light of the following specification when read in conjunction with the accompanying drawings.

BRIEF DESCRIPTION OF THE DRAWINGS

FIG. 1 is a perspective view of one embodiment of the diagnostic tool of the present invention;

FIG. 2 is an enlarged, partial view of a diagnostic tool for measuring horizontal fixation disparity;

FIG. 3 is an enlarged, partial view of a diagnostic tool for measuring vertical fixation disparity;

DETAILED DESCRIPTION OF THE PREFERRED EMBODIMENTS

Figure 4:
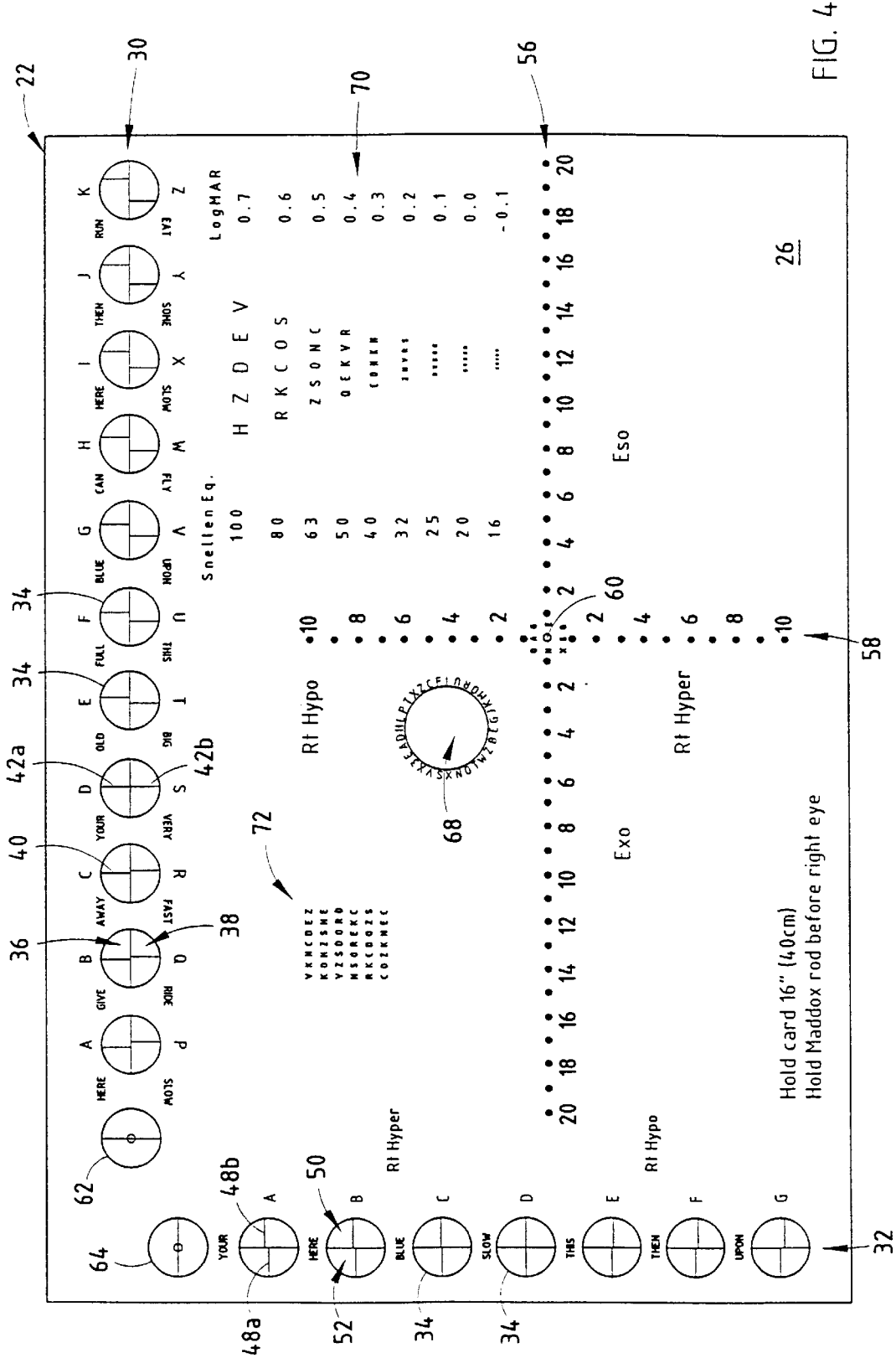
FIG. 4 is a plan view of the front side of the diagnostic card of FIG. 1.

The present invention will now be described with reference to the accompanying drawings wherein like reference numerals correspond to like elements in the several drawings. An oculomotor balance tester 20 according to one embodiment of the present invention is depicted in FIG. 1. Balance tester 20 includes a card 22 and additional components which may either be stand-alone components or be incorporated into a phoropter 24. The additional components comprise a Maddox rod and a pair of perpendicularly polarized lenses for placement in front of the patient's eyes. If these two items are not incorporated into phoropter 24, the Maddox rod could be a stand alone rod held by the patient, and the perpendicularly polarized lenses could be incorporated into a pair of glasses worn by the patient during testing. The Maddox rod is used in conjunction with a heterophoria test while the perpendicularly polarized lenses are used in conjunction with a fixation disparity test, as will be explained more fully below. Both of these tests are incorporated onto a front face 26 of card 22.

By measuring a patient's heterophoria and fixation disparity, such as via card 22, the present invention allows a practitioner to determine whether the patient's oculomotor system is in balance or not. The present invention recognizes that the amount and direction of fixation disparity is a good measure of how well the vergence and accommodative systems are coping with the stresses which might act to disrupt their proper function. Fixation disparity is the result of a process that integrates all of the stresses put on the binocular system and includes those stresses which result from its interaction with the accommodative system. In the majority of cases, the greatest predictable stress comes from the effort to overcome heterophoric misalignment. If the normal or expected effect of the heterophoria on fixation disparity can be accounted for, any remaining deviation from the expected amount is indicative of abnormality somewhere in the system. Therefore, if the fixation disparity is as expected for a particular amount of heterophoria, the oculomotor system must be sufficiently strong to support not only the stress due to that heterophoria, but also those stresses coming from any other source. In other words, the system must be in balance. Further details about the interactions of the accommodative and vergence systems are discussed in Chapter 5, entitled "Horizontal Prism Prescription" of the book *Clinical Uses of Prism: A Spectrum of Applications*, by Susan. A. Cotter (1995; ISBN: 0815118104), the disclosure of which is hereby incorporated herein by reference.

Card 22 enables a measurement of both fixation disparity and heterophoria to be obtained, and includes a graph 28 (FIG. 5) indicating the normal or expected relationship between a patient's fixation disparity and heterophoria. By comparing the patient's measured fixation disparity and heterophoria to graph 28, a practitioner can easily determine whether a patient's oculomotor system is in balance or not. Additional diagnostic tests are included on card 22 in order to differentially diagnose the oculomotor dysfunction should an abnormality be detected.

In practice, card 22 is preferably, although not necessarily, used after certain patient information, tests, and examinations have been discerned or performed, such as a patient case history, cover tests for binocularity at near and far distances, pupil examinations, a determination of near-point convergence, a measurement of accommodative amplitudes, version testing, and confrontation testing. When card 22 is used, it is also best used after the patient's refractive correction has been determined and is in place. Typically card 22 will be first used to measure a patient's horizontal and vertical heterophoria. After this measurement, the horizontal fixation disparity may be measured. The results of the horizontal fixation disparity and horizontal heterophoria are then evaluated to determine whether they bear a normal or expected relationship with respect to each other. If they bear a normal relationship, it may be concluded that the patient's disparity vergence and accommodative systems are in balance, although it may be desirable to further perform an accommodative facility test. If they do not bear a normal relationship, then it may be concluded that the patient's disparity vergence and accommodative systems are not in balance, and additional diagnostic tests are in order, some of which are also included on card 22, as will be discussed in more detail below.

In the embodiment of FIG. 1, oculomotor balance tester 20 is a near-point tester that tests a patient's balance at 16 inches (roughly 40 centimeters). It will be understood by those skilled in the art that card 22 could be adapted for measurements at other distances. Card 22 includes a test for both horizontal and vertical fixation disparity, as well as horizontal and vertical heterophoria. While it will be understood that other tests for fixation disparity and heterophoria can be used within the scope of the invention, the particular tests on card 22 include a modified Thorington test for heterophoria and a fixation disparity test similar to the one described in U.S. Pat. No. 4,222,639, issued to James Sheedy, the disclosure of which is hereby incorporated herein by reference.

The fixation disparity test includes a first set 30 and a second set 32 of a plurality of circles 34. First set 30 includes eleven circles 34 that are arranged horizontally generally across the top of front side 26 of card 22. Circles 34 of first set 30 are labeled A–K on card 22 adjacent their respective tops. Second set 32 includes seven circles 34 that arranged vertically generally along the left side of front 26 of card 22. Circles 34 of second set 32 are labeled A–G along their respective right sides. First set 30 is used to measure horizontal fixation disparity while second set 32 is used to measure vertical fixation disparity. As illustrated more clearly in FIG. 2, each circle 34 of first set 30 includes a top half 36 and a bottom half 38. Top and bottoms halves 36 and 38 are constructed out of polarizing material that are arranged such that top half 36 is perpendicularly polarized with respect to bottom half 36. An image 40 is positioned underneath top and bottom halves 36 and 38 and comprises vertical line segments 42a and 42b. Line segment 42a is positioned behind top half 36 and line segment 42b is positioned behind bottom half 38. Line segments 42a and 42b bear different vertical alignment relationships with respect to each other in each circle 34 of first set 30. The circle labeled D in first set 30 has line segments 42a and 42b vertically aligned, while circles E through K have top line segment 42a offset to the right in increasing progression with respect to bottom line segment 42b and A through C are offset to the left. Starting from circle A and moving to circle K, the offsets of vertical line segments 42a and 42b are 0.5, 0.2, 0.1, 0, 0.2, 0.5, 0.7, 0.9, 1.2, 1.6, and 2.1 millimeters, respectively.

First set 30 of circles 34 are used to measure a patient's fixation disparity by first placing perpendicularly polarized lenses in front of the patient's eyes. The perpendicularly polarized lenses can either be incorporated into phoropter 24, or they can be part of a pair of glasses worn by the patient, or other means. In the illustrated embodiment, the perpendicularly polarized lenses should be oriented so that the patient's left eye will only see bottom half 38 of each circle in first set 30 of circles 34 (due to the polarized material of bottom half 38), and the patient's right eye will only see top half 36 of each circle in first set 30 of circles 34 (due to the polarized material of top half 36). While the patient is looking through the polarized lenses, he or she is asked to determine in which circle vertical line segments 42a and 42b appear to be vertically aligned. As a focusing aid, the words HERE, GIVE, AWAY, YOUR, OLD, FULL, BLUE, CAN, HERE, THEN, and RUN are printed adjacent to the top of each circle. The amount of the patient's horizontal fixation disparity is determined by which circle he or she identifies as the one in which line segments 42a and b appear to be horizontally aligned.

A back side 44 of card 22 (FIG. 5) includes printed information indicating the measured amount of fixation disparity corresponding to the circle identified by the patient. The information is printed on the top side of a diffuser 46, which allows light to pass through back side 44 of card 22 into each circle 34 to thereby provide good illumination to each circle. For example, if the patient identifies circle D as the circle in which line segments 42a and b are aligned, the number 0 underneath the letter D on back side 44 indicates that there is no measurable horizontal fixation disparity. If the patient identifies circle I as the one with aligned segments 42a and b, then the patient has 10 minutes of arc of exo fixation disparity (10X where "X"

stands for exo). If the patient identifies the circle A as the one with aligned segments 42a and b, then the patient has 4 minutes of an arc of eso fixation disparity (4S where "S" stands for eso). The measured amount of fixation disparity for the remaining circles of first set 30 are also identified on back side 44 of card 22. Based on the patient's response, bracketing may be necessary to determine the amount of fixation disparity. For example, if the patient identifies circles A or B (4S and 2S, respectively) as being the best aligned, 3 then minutes or arc of eso fixation disparity should be recorded.

The test for fixation disparity may be carried out by placing a penlight about one centimeter behind each circle 34 in first set 30, starting with circle A and moving toward circle K, and asking the patient to first read the word adjacent the circle 34, and then look at the vertical line segments and indicate whether vertical line segments 42a and b appear to be aligned or not. Alternatively, a large light can be placed behind card 22 that illuminates all circles 34 simultaneously.

Card 22 further includes the letters P–Z printed upside-down and underneath the horizontal set 30 of circles 34. Adjacent each of these upside-down letters is an upside-down word. The card is meant to be turned upside-down when these words are read. Starting with the upside-down letter P and reading toward the upside-down Z, the upside-down words read as follows: SLOW, RIDE, FAST, VERY, BIG, THIS, UPON, FLY, SLOW, SOME, and EAT. The upside-down letters and words allow the test for horizontal fixation disparity to be performed while card 22 is held upside down, to thereby allow measurements of eso fixation disparity greater than 4 minutes of arc to be determined. As can be seen from back side 44, the largest eso fixation disparity that can be measured with card 22 held right-side up is 4 minutes of arc. By flipping card 22 upside-down, up to 18 minutes of eso fixation disparity can be measured. On back side 44 of card 22, the letters P–Z are positioned upside-down underneath diffuser 46. These letters indicate the measurement of horizontal heterophoria when card 22 is being used while upside-down. For example, if the patient identifies circle V as the one in which line segments 42a and b appear aligned while card 22 is upside down, the indication 6S next to circle V indicates the patient has six minutes of arc of horizontal eso fixation disparity. A corresponding measurement of fixation disparity is printed next to each other upside-down letter.

The measurement for vertical fixation disparity is performed via the second set 32 of circles 34. The circles in set 32 are vertically aligned along the left side of card 22 and measure vertical fixation disparity in a manner generally the same as that used to measure horizontal fixation disparity. In particular, each circle 34 of set 32 includes a pair of horizontal line segments 48a and b (FIG. 3). Each circle 34 is divided into a right half 50 and a left half 52 which are made out of polarized material that have the orientation of their polarization oriented perpendicularly with respect to each other. Thus, when a patient has polarizing lenses placed in front of their eyes, the patient's right eye will only see the image behind left half 52 of circle 34, which in this case reveals left line segment 48a. The patient's left eye will only see the image behind right half 52 of circle 34, which in this case reveals right line segment 48b. In the circle identified by the letter D, the horizontal line segments are vertically aligned. In the circles above and below the one identified by the letter D, right and left horizontal line segments 48a and b are misaligned to varying extents. Specifically, starting from circle A and moving down to circle G, the offsets of horizontal line segments 48a and b are as follows: 0.5, 0.2, 0.1, 0, 0.1, 0.2, and 0.5 millimeters, respectively.

The measurement of vertical fixation disparity is carried out by having the patient wear polarized lenses and asking him or her to identify in which of the circles 34 of second set 32 do the horizontal line segments 48a and b appear to be aligned. Back side 44 of card 22 tells the eye examiner how much vertical fixation disparity the patient has based upon the circle which the patient identifies. The measurements of vertical fixation disparity are printed on the back side 44 to the left of a vertical diffuser 54. For example, if the patient identifies circle A as the circle in which horizontal line segments 48a and b appear to be aligned, the number 4 adjacent the letter A on back side 44 indicates that the patient has 4 minutes of arc of right hyper fixation disparity. If the patient identifies the circle labeled F, then the patient has two minutes of arc of right hypo fixation disparity. The measurements of vertical fixation disparity for the remaining circles are found to the right of the corresponding letters on back side 44.

The test for heterophoria is carried out by utilizing the modified Thorington test. Specifically, this test involves a horizontal axis 56 and a vertical axis 58 which are printed on the front side 26 of card 22 (FIG. 4). Horizontal axis 56 and vertical axis 58 meet at an origin or pinhole 60 which is a transparent hole that allows light to pass through card 22 from back side 44 to front side 26. The horizontal heterophoria test is carried out by placing a penlight on back side 44 in front of pinhole 60 such that the light from the penlight shines through pinhole 60 and toward the patient. A Maddox rod is then held in front of the patient's right eye with the striations of the Maddox rod being horizontal in order to produce a vertical streak of light seen by the patient. A plurality of small letters are printed on front side 26 immediately surrounding pinhole 60 and the patient is asked to read one or more of these letters. After the patient has read one or more of these letters, he or she is asked to look directly at the bright light coming out of pinhole 60 and to report which number along horizontal axis 56 the vertical streak of light appears to pass through. Additionally, the patient is asked to identify on which side (right or left) of vertical axis 58 the vertical streak of light appears. This information identifies the patient's angular amount and direction of subjective, horizontal heterophoria measured in prism diopters. For example, if the patient identifies the vertical streak as appearing to pass through the number six to the right of vertical axis 58, then the patient has 6 diopters of subjective horizontal eso heterophoria.

The test for vertical heterophoria is carried out in the same manner using vertical axis 58. The Maddox rod placed in front of the patient's right eye is turned so that the light from the penlight passes through the Maddox rod and presents a horizontal streak to the patient's right eye. After focusing on the letter around pinhole 60, the patient is asked to look directly at the light coming out of pinhole 60 and indicate, while continuing to look at pinhole 60, where along vertical axis 58 the horizontal streak appears to pass through, and whether the streak is above or below horizontal axis 56. The numbers along vertical axis 58 indicate the amount and direction of the patient's subjective vertical heterophoria. For example, if the vertical streak appears above horizontal axis 56 and passing through the number 4, the patient has 4 diopters of subjective vertical right hypo heterophoria. The physical The physical spacing of each prism diopter on horizontal and vertical axes 56 and 58 are printed on card 22 approximately 0.16 inches apart.

Figure 5:
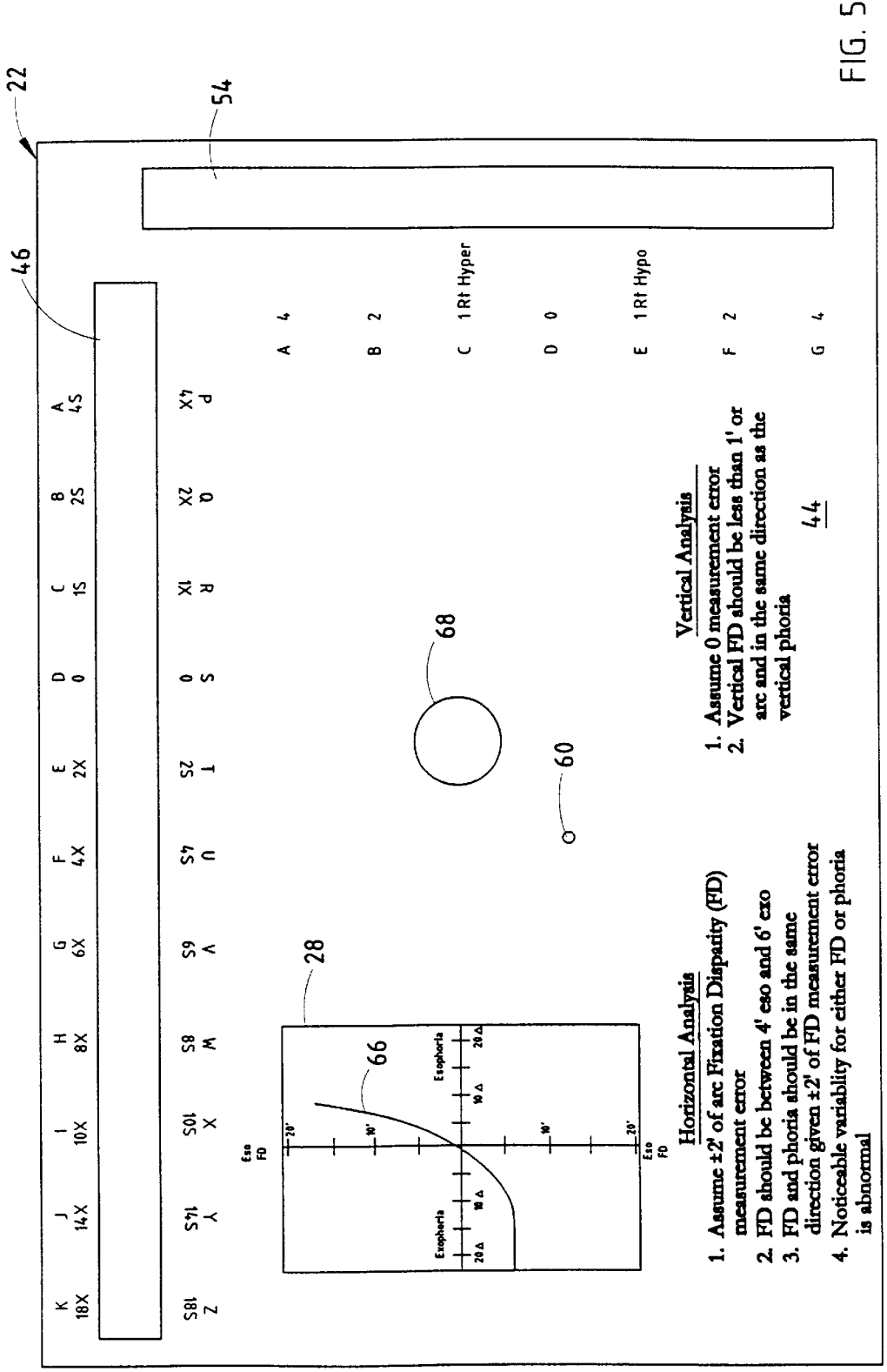
FIG. 5 is a plan view of the back side of the diagnostic card of FIG. 1.

After the patient's horizontal heterophoria and horizontal fixation disparity have been determined, the eye examiner next determines whether these two measurements bear a normal or abnormal relationship with respect to each other. This is accomplished by way of graph 28 on the back side 44 of card 22 (FIG. 5). Graph 28 includes an X-axis that corresponds to the amount and direction of the measured heterophoria, as measured in prism diopters. Graph 28 also includes a Y-axis that corresponds to the amount and direction of the measured fixation disparity, as measured in minutes of arc. A set of four instructions labeled "Horizontal Analysis" appears underneath graph 28 for properly interpreting and using graph 28. The first instruction states that plus/minus two minutes of an arc of fixation disparity should be assumed as a measurement error when using graph 28. The second instruction indicates that the amount of the patient's fixation disparity should be between four minutes of an arc eso and six minutes of an arc exo, not taking into account the measurement errors. When taking into account measurement errors, the actual measured values of the patient's fixation disparity should be between 6 minutes of arc eso and eight minutes of arc exo. If the measured fixation disparity exceeds either of these limits, central suppression must be occurring and an oculomotor imbalance exists. The imbalance is greater the more the fixation disparity exceeds these limits. Where such an imbalance exists, additional diagnostic tests are warranted.

The third instruction states that the fixation disparity and heterophoria should be in the same direction, given the measurement errors for fixation disparity. Graph 28 includes a line 66 that describes the amount and direction of fixation disparity that should accompany a certain amount and direction of heterophoria, if the oculomotor system is operating in a normal fashion. For a given amount and direction of heterophoria, the fixation disparity should be within plus/minus two minutes of arc of the fixation disparity attendant to that heterophoria. For example, a two prism diopter exophore should have a fixation disparity of approximately two minutes of arc exo according to line 66. The measured amount of fixation disparity should therefore be between zero and four minutes of arc exo. As another example, a four prism diopter exophore should have a measured fixation disparity of between one and five minutes of arc exo. Any amount of exophoria above six diopters should be accompanied by a measured amount of fixation disparity between four and eight minutes of arc exo. The range of acceptable fixation disparities for a given heterophoria accommodates the normal measurement variation in both the fixation disparity and the heterophoria measurements. However, if repeated measures of fixation disparity are greater than four minutes of arc eso or six minutes or arc exo, even allowing for measurement error, the eye examiner should be alerted that the probability of an oculomotor imbalance has increased.

The fourth instruction underneath graph 28 explains that if the patient notices sufficient movement of the measurement lines to cause the patient to comment on that movement, the probability of oculomotor imbalance increases.

Card 22 includes further instructions labeled "Vertical Analysis" for use in analyzing the relationship between the patient's vertical fixation disparity and vertical heterophoria. In general, the vertical fixation disparity test needs only to be performed if the patient has first reported a vertical phoria from the heterophoria test, or if there are other unexplained symptoms. The first instruction states that no measurement error should be assumed for the vertical analysis. The second instruction states that the vertical fixation disparity should be less than one minutes of an arc and in the same direction as the vertical phoria for a normal system If not, then a vertical imbalance exists. Additionally, if the patient reports any vertical heterophoria greater than ortho plus/minus 0.5 prism diopters, then a vertical imbalance is present.

If the foregoing tests indicate that the patient's accommodative and vergence systems are not in balance, additional diagnostic tests are in order, such as those listed in the following chart.

| CONDITION | NORMAL RESULTS | SPECIFIC TESTS |
|---|---|---|
| Distance horizontal phoria | Between 1 Δeso and 4 Δexo. | Distance vergence facility<br>Risley vergences<br>Forced vergence cover test for latent exophoria<br>Delayed/cyloplegic refraction<br>Anisophoria testing<br>Aniseikonia testing |
| Near horizontal phoria | Coordinated with fixation disparity | Near vergence facility<br>Risley vergences<br>Accommodative lag<br>Binocular cross cylinder<br>Forced vergence cover test for latent exophoria<br>Forced vergence fixation disparity curve<br>Anisophoria testing |
| Near fixation disparity | Between 4' eso and 6' exo | Recheck near horizontal phoria<br>Near vergence facility<br>Risley vergences<br>Test for fine stereopsis<br>Forced vergence fixation disparity curve<br>Test for fine suppression (Pola-Mirror, Bar Reader)<br>MKM<br>CA/C determination<br>Aniseikonia test |
| Computed Near/Far AC/A | Between 3/1 and 5/1 | Gradient AC/A<br>Kinetic cover test |
| Near vertical phoria | <1Δ | Vertical fixation disparity amount and direction<br>Vertical vergences<br>Associated vertical phoria (Prism to neutralize vertical fixation disparity)<br>Cyclophoria |
| Binocular accommodative facility | ≧6 cycles in 30 seconds<br>≧5 cycles in 30 seconds if patient ≦12 years of age | Monocular accommodative facility (flipper, N/F)<br>PRA-NRA<br>Bell retinoscopy<br>Kinetic cover test |
| Pursuits | Only 1 fixation loss (one cycle in each of 4 meridians) | Test for optokinetic nystagmus<br>Doll's head reflex |
| Saccades | 1 or 2 undershoots, no overshoots (10 cycles) | Diagnostic Eye Movement (DEM) test<br>Electronic eye movement testing<br>Test for optokinetic nystagmus |

Of the tests listed in the above chart, the following can be performed with the help of card 22, as would be understood by one skilled in the art: Near vergence facility, accommodative lag, anisophoria testing, vertical vergences, associated vertical phoria, cyclophoria, and monocular accommodative facility. Accommodative and vergence facility tests are both able to be performed using card 22 by way of square block of letters 72 on front 26 of card 22.

Front side 26 of card 22 additionally includes tests for cyclophoria, dynamic retinoscopy, visual acuity, and associated heterophoria with or without central fusion lock. Eye examiners may find these tests useful in conjunction with the fixation disparity and heterophoria tests for oculomotor balance described above. Cyclophoria is measured by using the horizontal and vertical axes 56 and 58 of the modified Thorington test. A penlight is shined through pinhole 60 while the Maddox rod is positioned over the patient's right eye to create a horizontal streak of light. The patient is instructed to look at the penlight while the Maddox rod is rotated until the streak is seen exactly parallel to the row of numbers on horizontal axis 56. The cyclorotation is estimated in degrees from the position of the Maddox rod striations. Given that the Maddox rod is in front of the right eye, a counterclockwise (from the examiner's perspective) rotation of the Maddox rod would indicate a relative excyclorotation of the right eye.

Dynamic retinoscopy may be carried out by way of hole 68, which includes a series of letters and numbers printed about its circumference on front side 26 of card 22. While the card is held at the near-point position, the patient is asked to read the letters and numbers around hole 68 while the examiner performs Nott or MEM retinoscopy through hole 68.

Visual acuity can be measured by way of visual acuity chart 70 printed on the right side of front side 26. Visual acuity chart 70 (e.g., Bailey-Lovie type chart) includes 9 lines of letters of decreasing size starting from the top line and moving downward. The visual acuity can be recorded in the usual Snellen equivalent or with a logMAR (logarithm of the minimum angle of resolution) notation. If recorded with the logMAR notation, starting with the logMAR value of the previous or larger line, each letter read decreases (indicating better visual acuity) the logMAR amount by 0.2 log units. For instance, if the patient reads all of the letters on the 20/40 line and two of the letters on the 30/32 line, the logMAR designation would be 0.26 [0.3−(2×0.2)=0.26].

If it is desired to measure the patient's associated heterophoria with a central fusion lock, circles 62 and 64 can be used, the former being used for horizontal measurements and the latter being used for vertical measurements. Circle 62 includes aligned vertical segments 42a and b which include a small circle at their junction. Vertical segments 42a and b are each positioned behind perpendicularly oriented polarized material, as are circles 34 in horizontal set 30. While looking at segments 42a and b in circle 62, the patient is fused through successive amounts of either base-in or base-out prism until he or she reports subjective alignment of vertical segments 42a and b. If base-in prism is required to establish alignment, the associated heterophoria is exo in sign and the amount is the amount of prism needed to accomplish alignment. If base-out prism is required, the associated heterophoria is eso in sign. If the top segment 42a is seen by the patient to the right, this can be neutralized with base-out prism. If the top segment 42a is seen displaced to the left, this can be neutralized with base-in prism. The same procedure can be used to measure vertical heterophoria with fusion lock by using circle 64, which also includes a pair of perpendicularly polarized materials positioned in front of a pair of horizontally aligned line segments 48a and b.

If it is desired to measure the patient's associated heterophoria without a central fusion lock, the same procedure is used as described above for measurement with central fusion lock except that circle D in horizontal set 30 is used in place of circle 62 while circle D in vertical set is used in place of circle 64.

While the present invention has been described in terms of the preferred embodiments depicted in the drawings and discussed in the above specification, along with several alternative embodiments, it will be understood by one skilled in the art that the present invention is not limited to these particular embodiments, but includes any and all such modifications that are within the spirit and the scope of the present invention as defined in the appended claims.

What is claimed is:

1. A diagnostic tool for determining whether a patient's accommodative and vergence systems are in balance comprising:

a first test for measuring the patient's heterophoria;

a second test for measuring the patient's fixation disparity; and an instrument for determining whether the measured heterophoria and measured fixation disparity indicate that the patient's accommodative and vergence systems are in balance or not.

2. The diagnostic tool of claim 1 wherein said first test measures both vertical and horizontal heterophoria and said second test measures both vertical and horizontal fixation disparity.

3. A diagnostic tool for determining whether a patient's accommodative and vergence systems are in balance comprising:

a first test for measuring the patient's heterophoria;

a second test for measuring the patient's fixation disparity, said first and second tests being integrated onto a card; and an instrument for determining whether the measured heterophoria and measured fixation disparity indicate that the patient's accommodative and vergence systems al in balance or not.

4. A diagnostic tool for determining whether a patient's accommodative and vergence systems are in balance comprising:

a first test for measuring the patient's heterophoria, said first test for measuring heterophoria being a modified Thorington test;

a second test for measuring the patient's fixation disparity; and an instrument for determining whether the measured heterophoria and measured fixation disparity indicate that the patient's accommodative and vergence systems are in balance or not.

5. A diagnostic tool for determining whether a patient's accommodative and vergence systems are in balance comprising:

a first test for measuring the patient's heterophoria;

a second test for measuring the patient's fixation disparity, said first and second tests being near-point tests; and an instrument for determining whether the measured heterophoria and measured fixation disparity indicate that the patient's accommodative and vergence systems are in balance or not.

6. The tool of claim 5 wherein said instrument is a graph indicating an expected normal relationship between the measured heterophoria and the measured fixation disparity.

7. The diagnostic tool of claim 3 wherein said card further includes at least one additional test for refining the source of any imbalance between the patient's accommodative and vergence systems.

8. A diagnostic tool for determining whether a patient's accommodative and vergence systems are in balance comprising:

a base having a front surface;

a first test for measuring heterophoria positioned on the front surface of said base;

a second test for measuring fixation disparity positioned on the front surface of said base; and an instrument for determining whether the measured heterophoria and measured fixation disparity indicate that the patient's accommodative and vergence systems are in balance or not.

9. The diagnostic tool of claim 8 wherein said first test measures both vertical and horizontal heterophoria.

10. The diagnostic tool of claim 9 wherein said second test measures both vertical and horizontal fixation disparity.

11. The diagnostic tool of claim 10 wherein said instrument provides for separately determining whether said horizontal heterophoria and said horizontal fixation disparity bear a normal or abnormal relationship, and whether said vertical heterophoria and said vertical fixation disparity bear a normal or abnormal relationship.

12. A diagnostic tool for determining whether a patient's accommodative and vergence systems are in balance comprising:
a card having a front surface;
a first test for measuring heterophoria positioned on the from surface of said card;
a second test for measuring fixation disparity positioned on the front surface of said card; and
an instrument for determining whether the measured heterophoria and measured fixation disparity indicate that the patient's accommodative and vergence systems are in balance or not.

13. The diagnostic tool of claim 12 wherein said instrument comprises information printed on a back side of said card indicating an expected normal relationship between the measured heterophoria and the measured fixation disparity.

14. The diagnostic tool of claim 12 wherein said second test for measuring fixation disparity includes a plurality of areas containing first and second images positioned behind first and second polarized materials, said first and second polarized materials having perpendicular polarity, and said first and second images bearing different alignment relationships with each other for each area.

15. The diagnostic tool of claim 14 wherein a set of said plurality of areas are arranged in a horizontal row and said first and second polarized materials are positioned vertically above and below each other on said card, said set of areas being used to measure horizontal fixation disparity.

16. The diagnostic tool of claim 14 wherein a set of said plurality of areas are arranged in a vertical row and said first and second polarized materials are positioned horizontally side-by-side each other on said card, said set of areas being used to measure vertical fixation disparity.

17. The diagnostic tool of claim 12 wherein said card further includes at least one additional diagnostic visual test, such as, but not limited to, a visual acuity test.

18. The diagnostic tool of claim 12 wherein said card further includes a dynamic retinoscopy test.

19. The diagnostic tool of claim 12 wherein said card further includes a prescriptive test for fixation disparity neutralization with a central fusion lock.

20. A diagnostic tool for determining whether a patient's accommodative and vergence systems are in balance comprising:
a card having a front surface;
a first test for measuring heterophoria positioned on the front surface of said card, said first test for measuring heterophoria being a modified Thorington test;
a second test for measuring fixation disparity positioned on the front surface of said card; and
an instrument for determining whether the measured heterophoria and measured fixation disparity indicate that the patient's accommodative and vergence systems are in balance or not.

21. A method for determining a patient's oculomotor balance comprising:
measuring the amount of the patient's heterophoria;
measuring the amount of the patient's fixation disparity;
determining whether the measured amount of the patient's fixation disparity is normal for the measured amount of heterophoria; and
concluding that the patient's oculomotor system is out of balance if said measured amount of fixation disparity is not normal for the measured amount of heterophoria.

22. The method of claim 21 wherein said heterophoria and fixation disparity are measured for near-point distances.

23. A method for determining a patient's oculomotor balance comprising
providing a card and placing tests for heterophoria and fixation disparity onto said card;
measuring the amount of the patient's heterophoria;
measuring the amount of the patient's fixation disparity;
determining whether the measured amount of the patient's fixation disparity is normal for the measured amount of heterophoria; and
concluding that the patient's oculomotor system is out of balance if said measured amount of fixation disparity is not normal for the measured amount of heterophoria.

24. The method of claim 23 further including providing a graph on said card indicating a normal relationship between fixation disparity and heterophoria.

25. The method of claim 23 further including providing at least one additional visual diagnostic test on said card.

26. The method of claim 25 wherein said at least one additional visual diagnostic test includes a visual acuity test.

27. The method of claim 25 wherein said at least one additional visual diagnostic test includes a dynamic retinoscopy test.

28. A method for determining a patient's oculomotor balance comprising:
measuring the amount of the patient's heterophoria using a modified Thorington technique;
measuring the amount of the patient's fixation disparity;
determining whether the measured amount of the patient's fixation disparity is normal for the measured amount of heterophoria; and
concluding that the patient's oculomotor system is out of balance if said measured amount of fixation disparity is not normal for the measured amount of heterophoria.

* * * * *

UNITED STATES PATENT AND TRADEMARK OFFICE
CERTIFICATE OF CORRECTION

PATENT NO. : 6,644,811 B2  Page 1 of 1
APPLICATION NO. : 09/832555
DATED : November 11, 2003
INVENTOR(S) : Jimmie James Saladin It is certified that error appears in the above-identified patent and that said Letters Patent is hereby corrected as shown below:

<u>Column 10:</u>
Line 26, Claim 3, "al" should be --are--.

<u>Column 11:</u>
Line 20, Claim 12, "from" should be --front--.

Signed and Sealed this

Fifth Day of February, 2008

JON W. DUDAS
*Director of the United States Patent and Trademark Office*